US012727815B2

(12) United States Patent
Liu et al.

(10) Patent No.: US 12,727,815 B2
(45) Date of Patent: Sep. 8, 2026

(54) METHOD FOR MONITORING SLEEP, APPARATUS, DEVICE, AND STORAGE MEDIUM

(71) Applicant: Guangdong COROS Sports Technology Joint Stock Company, Dongguan (CN)

(72) Inventors: Naixi Liu, Dongguan (CN); Zhengguo Cai, Dongguan (CN); Xin Liu, Dongguan (CN)

(73) Assignee: GUANGDONG COROS SPORTS TECHNOLOGY JOINT STOCK COMPANY, Dongguan (CN)

( * ) Notice: Subject to any disclaimer, the term of this patent is extended or adjusted under 35 U.S.C. 154(b) by 148 days.

(21) Appl. No.: 18/360,336

(22) Filed: Jul. 27, 2023

(65) Prior Publication Data

US 2024/0032858 A1 Feb. 1, 2024

(30) Foreign Application Priority Data

Jul. 28, 2022 (CN) ......................... 202210896687.6

(51) Int. Cl.
*A61B 5/00* (2006.01)

(52) U.S. Cl.
CPC .......... *A61B 5/4809* (2013.01); *A61B 5/7282* (2013.01)

(58) Field of Classification Search
CPC ............................ A61B 5/4809; A61B 5/7282
USPC ......................................................... 600/300
See application file for complete search history.

(56) References Cited

U.S. PATENT DOCUMENTS 12,223,877 B2 2/2025 Li et al.
2007/0216610 A1 9/2007 Smith
2017/0143252 A1 5/2017 Zou
2020/0147376 A1* 5/2020 Dieken .............. A61N 1/36139
2020/0205728 A1* 7/2020 Molina ............... A61B 5/4815
(Continued)

FOREIGN PATENT DOCUMENTS

CN 103968506 A 8/2014
CN 109937010 A 6/2019
(Continued)

OTHER PUBLICATIONS

Extended Search Report for European Application No. 23176821.9-1113, dated Jan. 12, 2024 (7 pages).
(Continued)

*Primary Examiner* — Nicole F Johnson
(74) *Attorney, Agent, or Firm* — Michael Best & Friedrich LLP

(57) ABSTRACT

Provided are a method for monitoring sleep, an apparatus, a device, and a storage medium. The method includes the steps described below. Sleep monitoring for a user is started and sleep monitoring data is acquired. According to the sleep monitoring data, whether the user enters a first sleep is determined. According to the sleep monitoring data, whether the user ends the first sleep is determined in the case where it is determined that the user enters the first sleep. End time of the first sleep is acquired in the case where it is determined that the user have ended the first sleep, and the end time of the first sleep is time when the user ends the first sleep. The sleep monitoring is ended in the case where it is not identified that the user enters a second sleep within a first duration from the end time of the first sleep.

17 Claims, 3 Drawing Sheets

(56) References Cited

U.S. PATENT DOCUMENTS

| | | | |
|---|---|---|---|
| 2021/0138661 | A1 | 5/2021 | Kim |
| 2022/0104704 | A1 | 4/2022 | Zakharov |
| 2022/0277689 | A1 | 9/2022 | Zhao et al. |
| 2022/0301489 | A1 | 9/2022 | Wang et al. |

FOREIGN PATENT DOCUMENTS

| | | | |
|---|---|---|---|
| CN | 110584611 | A | 12/2019 |
| CN | 115316950 | A | 11/2022 |
| WO | 2021190538 | A1 | 9/2021 |
| WO | 2022021707 | A1 | 2/2022 |

OTHER PUBLICATIONS

European Patent Office Action for Application No. 23176821.9 dated Oct. 7, 2025 (6 pages).

Chinese Patent Office Action for Application No. 20210896687.6 dated Mar. 20, 2026 (8 pages including partial English machine translation).

Wang, "The Research of Cross-Layer Networking Protocol for Asynchronous Wireless Sensor Networks", University of Science and Technology of China, dissertation dated May 2, 2011 (116 pages including English Abstract).

Chinese Patent Office Action for Application No. 20210896687.6 dated Jun. 13, 2026 (16 pages including English machine translation).

* cited by examiner

METHOD FOR MONITORING SLEEP, APPARATUS, DEVICE, AND STORAGE MEDIUM

CROSS-REFERENCE TO RELATED APPLICATION(S)

This application claims priority to Chinese Patent Application No. 202210896687.6 filed Jul. 28, 2022, the disclosure of which is incorporated herein by reference in its entirety.

TECHNICAL FIELD

The present invention relates to the technical field of sleep monitoring and, in particular, to a method for monitoring sleep, an apparatus, a device, and a storage medium.

BACKGROUND

Sleep monitoring technology is widely used in wearable devices for tracking the sleep process of the human body, giving a temporal determination of sleep and identifying stages of sleep. The determination of sleep and identification of each stage are generally performed by collection of data related to sleep and utilization of inconsistent data characteristics between sleep and non-sleep and among different sleep stages.

However, the process of determination and identification requires the data acquisition module of the sleep monitoring device to be continuously started to capture sleep information in time. This process, since it cannot be interrupted, continues to consume power. In the related methods for monitoring sleep, to ensure the accuracy of monitoring results, the data acquisition module is usually kept working. Therefore, most sleep monitoring devices require high power consumption and have a short service time.

SUMMARY

The present invention provides a method for monitoring sleep, an apparatus, a device, and a storage medium to reduce the power consumption of the device under the condition of ensuring the accuracy of sleep monitoring results.

According to an aspect of the present invention, a method for monitoring sleep is provided. The method includes the steps described below.

Sleep monitoring for a user is started and sleep monitoring data is acquired.

According to the sleep monitoring data, whether the user enters a first sleep is determined.

According to the sleep monitoring data, whether the user ends the first sleep is determined in the case where it is determined that the user enters the first sleep.

End time of the first sleep is acquired in the case where it is determined that the user have ended the first sleep, and the end time of the first sleep is time when the user ends the first sleep.

The sleep monitoring is ended in the case where it is not identified that the user enters a second sleep within a first duration from the end time of the first sleep.

According to another aspect of the present invention, a sleep monitoring apparatus is provided, which includes at least one processor configured to perform the following steps:

Sleep monitoring for a user is started and sleep monitoring data is acquired.

According to the sleep monitoring data, whether the user enters a first sleep is determined.

According to the sleep monitoring data, whether the user ends the first sleep is determined in the case where it is determined that the user enters the first sleep.

End time of the first sleep is acquired in the case where it is determined that the user have ended the first sleep, and the end time of the first sleep is time when the user ends the first sleep.

The sleep monitoring is ended in the case where it is not identified that the user enters a second sleep within a first duration from the end time of the first sleep.

According to another aspect of the present invention, an electronic device is provided. The electronic device includes at least one processor and a memory.

The memory is in a communication connection with the at least one processor.

The memory stores a computer program executable by the at least one processor. The computer program is configured to, when executed by the at least one processor, cause the at least one processor to execute the method for monitoring sleep described in any embodiment of the present invention.

According to another aspect of the present invention, a non-transitory computer-readable storage medium is provided, which is configured to store computer instructions for implementing the method for monitoring sleep described in any embodiment of the present invention when the computer instructions are executed by a processor.

Embodiments of the present invention provide a method for monitoring sleep, the steps of which are described below. Sleep monitoring for a user is started and sleep monitoring data is acquired. According to the sleep monitoring data, whether the user enters a first sleep is determined. According to the sleep monitoring data, whether the user ends the first sleep is determined in the case where it is determined that the user enters the first sleep. End time of the first sleep is acquired in the case where it is determined that the user have ended the first sleep, and the end time of the first sleep is time when the user ends the first sleep. The sleep monitoring is ended in the case where it is not identified that the user enters a second sleep within a first duration from the end time of the first sleep. The method for monitoring sleep provided by embodiments of the present invention formulates rules for turning on and off the sleep monitoring and sets a determination method for a user's sleep. In this manner, for the device, power consumption is reduced and service time is prolonged under the condition of ensuring the accuracy of monitoring results.

It is to be understood that the contents described in this part are not intended to identify key or important features of embodiments of the present invention and are not intended to limit the scope of the present invention. Other features of the present invention are readily understood through the description hereinafter.

BRIEF DESCRIPTION OF DRAWINGS

To illustrate solutions in embodiments of the present invention more clearly, the accompanying drawings used in description of the embodiments are briefly described below. Apparently, the accompanying drawings described below illustrate part of embodiments of the present invention, and those of ordinary skill in the art may obtain other accompanying drawings based on the accompanying drawings described below on the premise that no creative work is done.

DETAILED DESCRIPTION

The solutions in embodiments of the present invention are described clearly and completely in conjunction with drawings in the embodiments of the present invention from which the solutions are better understood by those skilled in the art. Apparently, the embodiments described below are part, not all, of the embodiments of the present invention. Based on the embodiments described herein, all other embodiments obtained by those skilled in the art on the premise that no creative work is done are within the scope of the present invention.

It is to be noted that terms such as “first” and “second” in the description, claims, and drawings of the present invention are used to distinguish between similar objects and are not necessarily used to describe a particular order or sequence. It should be understood that the data used in this manner are interchangeable where appropriate so that the embodiments of the present invention described herein may also be implemented in a sequence not illustrated or described herein. In addition, terms “comprising”, “including”, and any other variations thereof are intended to encompass a non-exclusive inclusion. For example, a process, method, system, product, or device that includes a series of steps or units not only includes the expressly listed steps or units, but may also include other steps or units that are not expressly listed or are inherent to such a process, method, product, or device.

Figures 1, 2:
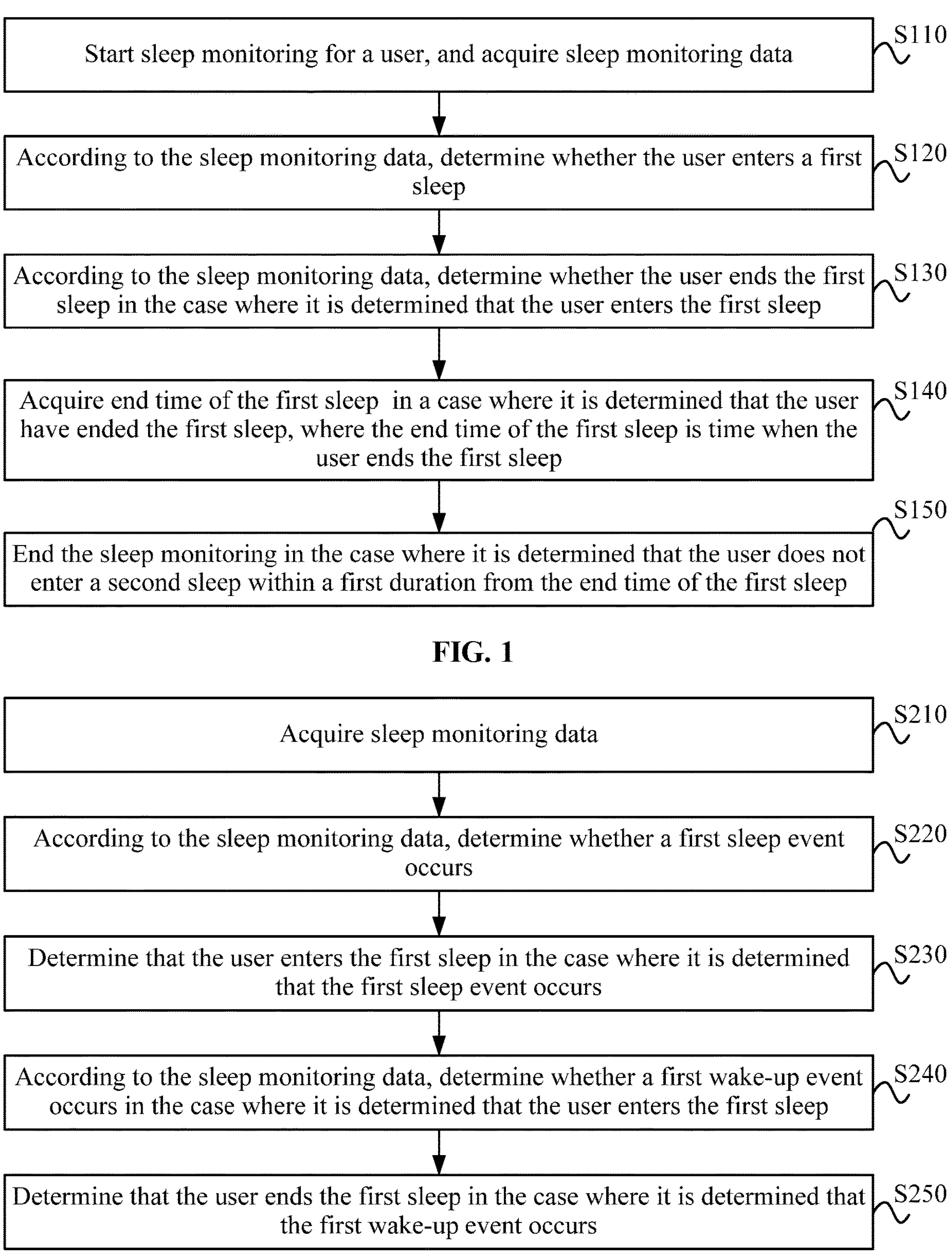
FIG. 1 is a flowchart of a method for monitoring sleep according to embodiments of the present invention.
FIG. 2 is a flowchart of another method for monitoring sleep according to embodiments of the present invention.

FIG. 1 is a flowchart of a method for monitoring sleep according to embodiments of the present invention. This embodiment is applicable to monitoring a user’s sleep conditions. The method may be executed by a sleep monitoring apparatus. The apparatus may be implemented in the form of software and/or hardware. The apparatus may be configured in an electronic device. As shown in FIG. 1, the method includes the steps described below.

S110: Sleep monitoring for a user is started, and sleep monitoring data is acquired.

The user monitors sleep by using the sleep monitoring apparatus provided in this embodiment. The sleep monitoring data is related to sleep conditions of the user, such as sign data and motion data.

Preferably, the sleep monitoring data may include acceleration data and heart rate related data. The acceleration data can reflect whether the user is in an active state. The heart rate related data may include heartbeat frequency data and heart rate variability data, which may reflect user signs.

In some embodiments, sleep monitoring for a user may be actively started by the user or automatically started at a set time according to a preset condition. The sleep monitoring data may be acquired by a corresponding data acquisition apparatus according to different sleep monitoring data. For example, the acceleration data may be acquired by using an accelerometer.

The heart rate related data may be acquired by a photoplethysmography (PPG) acquisition apparatus. In other words, the photoelectric sensor is used to detect the difference in the intensity of reflected light absorbed by human blood and tissue to trace the change of blood vessel volume in the cardiac cycle so that the heart rate is calculated from the obtained pulse waveform.

Preferably, the accelerometer and the PPG acquisition apparatus may be integrated in the sleep monitoring apparatus provided by this embodiment.

S120: According to the sleep monitoring data, whether the user enters a first sleep is determined.

In some embodiments, the sleep condition of the user can be determined according to the acquired sleep monitoring data, that is, whether the user is in the first sleep or the awake state. For example, if it can be determined according to the sleep monitoring data that the user is still and the heart rate drops to a set threshold, it can be considered that the user enters the first sleep.

S130: According to the sleep monitoring data, whether the user ends the first sleep is determined in the case where it is determined that the user enters the first sleep.

Similar to the preceding step, when the user is in the first sleep, it can be determined whether the first sleep is ended or not according to the acquired sleep monitoring data. For example, if it is determined according to the sleep monitoring data that the user has an action, or the heart rate is raised to a set threshold, it may be considered that the user ends the first sleep.

S140: End time of the first sleep is acquired when the user ends the first sleep in the case where it is determined that the user have ended the first sleep.

The end time of the first sleep indicates that after the sleep monitoring is started, it is detected that the user enters the sleep for the first time, and the sleep ends after a period of time.

In some embodiments, after the user enters the first sleep for the first time, it is determined according to the sleep monitoring data that the user’s first sleep ends, and the time when the corresponding sleep monitoring data reaches the set threshold may be determined as the end time of the first sleep.

S150: The sleep monitoring is ended in the case where it is not identified that the user enters a second sleep within a first duration from the end time of the first sleep.

In some embodiments, after the user ends the first sleep, sleep monitoring may be continued for the user. The duration of the continuous monitoring may be a first set duration from the end time of the first sleep. The sleep monitoring is ended if it is not identified that the user enters the second sleep during the continuous monitoring time. The first sleep differs from the second sleep in the occurrence time. The first sleep is the sleep detected for the first time. The second sleep is the sleep detected within the first preset time after the end of the first sleep. The sleep monitoring may be stopped by turning off each data acquisition apparatus configured for acquiring sleep monitoring data and stopping operations such as data acquisition, data analysis, and data recording. The sleep monitoring is ended after the user ends the sleep state again if it is identified that the user enters the sleep again during the continuous monitoring time.

Optionally, the method also includes the steps described below. Start time of the first sleep is acquired, and the start time of the first sleep is time when the user enters the first sleep. A first sleep duration is determined according to the start time of the first sleep and the end time of the first sleep. A first duration is determined according to the first sleep duration.

Further, the method also includes the steps described below.

Start time of the first sleep is acquired. A first sleep duration is determined according to the start time of the first sleep and the end time of the first sleep. A first set duration is determined according to the first sleep duration.

The start time of the first sleep is the time when it is detected that the user enters the sleep for the first time after the sleep monitoring is started. The time between the start time of the first sleep and the end time of the first sleep is the sleep duration after the user enters the sleep for the first time when the sleep monitoring is started once.

In some embodiments, start time of the first sleep is acquired. A first sleep duration is determined according to the start time of the first sleep and the end time of the first sleep. A first duration is determined according to the first sleep duration. For example, when the duration of the first sleep is longer, it may be considered that the user is less likely to fall asleep again, and the first duration is thus set to a smaller value. When the duration of the first sleep is shorter, it may be considered that the user may fall asleep again after the end of the first period of sleep, and the time for continuous monitoring may be prolonged.

Optionally, the method of determining the first duration according to the first sleep duration may be determining a difference between a preset third duration and the first sleep duration as the first duration when the first sleep duration is less than a preset second duration.

Specifically, when the duration of the first sleep is shorter, a preset second duration may be used as the reference value, and the difference between the second duration from the start time of the first sleep and the duration of the first sleep is used as the first set duration for continuous monitoring.

Specifically, the method of determining the first duration according to the first sleep duration may be determining a duration set by a system or the user as the first duration when the first sleep duration is greater than or equal to a preset second duration.

For example, if the first sleep duration is greater than or equal to 6 hours, the duration of 1 hour set by the system or the user may be determined as the first duration, which means to continue monitoring for 1 hour after the end of the user's first sleep is detected. If the first sleep duration is less than 6 hours (taking 5 hours as an example), and the second set duration is made to be 8 hours, the first set duration is the difference between 8 hours and the first sleep duration, which means to continue monitoring for 3 hours after it is detected that the user ends the first sleep.

Specifically, the user may set the duration of continuous monitoring after the end of the first sleep. For example, the first set duration may be set to 1 hour, that is, the monitoring continues for 1 hour after the end of the user's first sleep. If it is not identified that the user enters the sleep again within the 1 hour, the sleep monitoring is ended.

FIG. 2 is a flowchart of a method for monitoring sleep according to embodiments of the present invention. The method is another possible implementation of the preceding embodiment. As shown in FIG. 2, the method includes the steps described below.

S210: Sleep monitoring data is acquired.

In some embodiments, the sleep monitoring data may be acquired by a corresponding data acquisition apparatus according to different sleep monitoring data.

S220: According to the sleep monitoring data, whether a first sleep event occurs is determined.

The first sleep event is an event in which the state of the user changes from the awake state to the sleep state.

In some embodiments, the current state of the user, that is, whether the user is awake or asleep, can be determined according to the sleep monitoring data. When it is first detected that the state of the user changes from being awake to being asleep, it can be determined that the first sleep event occurs.

Optionally, whether the first sleep event occurs is determined according to the sleep monitoring data. The manner of determination may be the following: Whether the user sleeps is determined according to the sleep monitoring data; it is determined that a sleep event occurs in the case where the user falls asleep.

Specifically, the sleep monitoring data may include acceleration data acquired by an accelerometer. The condition for determining that the user falls asleep may be determining that the user is still and inactive for a period of time according to the acceleration data. The sleep monitoring data may include displacement data acquired by a positioning apparatus. The condition for determining that the user falls asleep may be that the displacement of the user within a period of time is determined to be less than a set threshold according to the displacement data. The sleep monitoring data may include heart rate and heart rate variability data acquired by the PPG acquisition apparatus. The condition for determining that the user falls asleep may be that the heart rate of the user over a period of time is determined to be less than a set threshold according to the heart rate and heart rate variability data. Further, the sleep monitoring data may be one or more of the preceding several types of data, and the condition for determining that the user falls asleep may be one or a combination of the preceding several conditions. For example, the condition for determining that the user falls asleep may be that the user is inactive for a period of time, the displacement is less than a set threshold, and the heart rate is less than a set threshold.

Preferably, a standard data model may be established in advance. In other words, a large amount of previous data may be acquired and classified. The sleep monitoring data may be divided into four types, namely, wakefulness, rapid eye movement, deep sleep, and light sleep. Each classified data set has its characteristics. When whether the user falls asleep is determined, the currently acquired sleep monitoring data is compared with the standard data set, and the sleep monitoring data closest to the four tags is selected and marked as the sleep stages corresponding to the tags.

Specifically, the acceleration data, the heart rate data, and the heart rate variability data are used as an example. The acceleration data, the heart rate data, and the heart rate variability data have different characteristics in each sleep stage. In the order of wakefulness, rapid eye movement, light sleep, and deep sleep, the acceleration data decreases in sequence, the heart rate data decreases in sequence, and the heart rate variability data increases in sequence. According to this characteristic, each sleep stage has corresponding three-dimensional acceleration, heart rate, and heart rate variability data. Based on this, different sleep stages can be identified.

Preferably, to reduce power consumption, within the time period in which the sleep monitoring is started, a possible sleep state may first be identified by the accelerometer, and then the PPG data acquisition apparatus is started. If the accelerometer identifies that the user is active, the PPG data acquisition apparatus is not started. After the PPG data acquisition apparatus is started, if the accelerometer again identifies that the user is active, the PPG data acquisition apparatus continues to be turned off, and the process is repeated continuously.

Further, whether a sleep event occurs is determined according to the sleep monitoring data. The manner of determination may be the following: Whether the user sleeps is determined according to the sleep monitoring data. Whether the user wakes up is determined according to the sleep monitoring data in the case where it is determined that the user falls asleep. It is determined that a sleep event occurs in the case where it is not detected that the user wakes up within a third set duration from the time when the user falls asleep.

In some embodiments, to prevent misjudgment, it may not be immediately determined that the sleep event occurs when it is detected that the sleep monitoring data is in a sleep range, but it is determined whether the sleep monitoring data are all in the sleep range within a preset fourth duration. It is determined that the first sleep event occurs in the case where it is determined that the sleep monitoring data are all within the sleep range within the preset fourth duration.

S230: It is determined that the user enters the first sleep in the case where it is determined that the first sleep event occurs.

In some embodiments, start time of the first sleep event and time of occurrence of the first sleep event determined are acquired in the case where it is determined that the first sleep event occurs.

Specifically, start time of the first sleep is determined according to the start time of the first sleep event and the time of the occurrence of the first sleep event determined. The start time of the first sleep is a time between the start time of the first sleep event and the time of the occurrence of the first sleep event determined.

S240: According to the sleep monitoring data, whether a first wake-up event occurs is determined in the case where it is determined that the user enters the first sleep.

Specifically, whether the sleep monitoring data are all in an awake range within a preset fifth duration is determined. It is determined that the first wake-up event occurs in the case where it is determined that the sleep monitoring data are all within the awake range within the preset fifth duration.

The first wake-up event is an event in which the state of the user changes from the sleep state to the awake state after the user enters the first sleep during the sleep monitoring.

In some embodiments, the current state of the user, that is, whether the user is awake or asleep, can be determined according to the sleep monitoring data. When it is detected that the state of the user changes from being asleep to being awake, it can be determined that the first wake-up event occurs.

Optionally, whether the first wake-up event occurs is determined according to the sleep monitoring data. The manner of determination may be the following: Whether the user wakes up is determined according to the sleep monitoring data; it is determined that a wake-up event occurs in the case where the user wakes up.

Specifically, the end time of the first sleep is determined according to the start time of the first wake-up event and time of occurrence of the first wake-up event determined. The end time of the first sleep is a time between the start time of the first wake-up event and the time of the occurrence of the first wake-up event determined.

Specifically, similar to the determination of the sleep event, the sleep monitoring data may include acceleration data acquired by an accelerometer. The condition for determining that the user wakes up may be determining that the user makes an action according to the acceleration data. The sleep monitoring data may include displacement data acquired by a positioning apparatus. The condition for determining that the user wakes up may be that the displacement of the user within a period of time is determined to be greater than or equal to a set threshold according to the displacement data. The sleep monitoring data may include heart rate and heart rate variability data acquired by the PPG acquisition apparatus. The condition for determining that the user wakes up may be that the heart rate of the user over a period of time is determined to be greater than or equal to a set threshold according to the heart rate and heart rate variability data. Further, the sleep monitoring data may be one or more of the preceding several types of data, and the condition for determining that the user wakes up may be one or a combination of the preceding several conditions. For example, the condition for determining that the user wakes up may be that the user makes an action, or the displacement within a period of time is greater than or equal to the set threshold, or the heart rate is greater than or equal to the set threshold.

Preferably, a standard data model may be established as well. When whether the user wakes up is determined, the currently acquired sleep monitoring data is compared with the standard data set. According to different characteristics of the data sets corresponding to the four tags of wakefulness, rapid eye movement, light sleep, and deep sleep, the sleep monitoring data closest to the four tags is selected and marked as the sleep stages corresponding to the tags.

Optionally, whether the first wake-up event occurs is determined according to the sleep monitoring data. The manner of determination may be the following: Whether the user wakes up is determined according to the sleep monitoring data; it is determined that the first wake-up event does not occur in the case where it is determined that the user wakes up, and it is detected that the user, after waking up, falls asleep within the fourth set duration.

In some embodiments, the user may enter sleep again after being awake for a short time. To prevent misjudgment, a fourth set duration may be set as a buffer period. When it is detected that the user wakes up, if the user continues to be awake within the fourth set duration, that is, it is detected that the user, after waking up, falls asleep within the fourth set duration, it can be determined that the first wake-up event does not occur, that is, the user does not end the first sleep.

Further, the method also includes the steps described below.

The first wake-up time of the first wake-up event is acquired.

Correspondingly, the end time of the first sleep may be acquired by the following method:

The first wake-up time is determined as the end time of the first sleep.

In some embodiments, the first wake-up time when the first wake-up event occurs may be acquired, and the first wake-up time is determined as the end time of the first sleep.

S250: It is determined that the user have ended the first sleep in the case where it is determined that the first wake-up event occurs.

In some embodiments, according to the method for determining the first wake-up event provided in the preceding steps, if it is determined that the first wake-up event occurs, it can be determined that the user ends the first sleep.

Further, the method also includes the steps described below.

Whether the user ends the second sleep is determined according to the sleep monitoring data in the case where it is identified that the user enters the second sleep within the first set duration from the end time of the first sleep. The sleep monitoring is ended in the case where it is identified that the user ends the second sleep within the first set duration.

Optionally, during sleep monitoring of the user, when the user ends the sleep for the first time, the user may continue to be monitored within the first set duration. If it is identified that the user enters sleep again during this period, the user continues to be monitored until the end of the second sleep, and the sleep monitoring is ended when the end of the second sleep is identified. Preferably, when it is identified that the user has a second wake-up event, that is, a change from the sleep state to the awake state for the second time, it is determined that the second sleep of the user ends. Further, within the buffer period of the set duration, if the user continues to be awake, it can be determined that the second sleep ends.

Optionally, the determination of the second sleep event and the second wake-up event is the same as that of the first sleep event and the second sleep event.

Further, the method also includes the steps described below.

The sleep monitoring is ended in the case where it is not identified that the user enters a second sleep within a first set duration from the end time of the first sleep.

Optionally, during sleep monitoring of the user, when the user ends the sleep for the first time, the user may continue to be monitored within the first duration. If it is not identified that the user enters the sleep again during this period, the sleep monitoring can be stopped.

Further, the method also includes the step described below.

A set start time for conventional sleep monitoring is acquired.

Correspondingly, enabling the sleep monitoring for the user includes enabling the sleep monitoring for the user at the start time of the conventional sleep monitoring.

Optionally, start time of the conventional sleep monitoring may be configured according to the user's habit. At the start time, the sleep monitoring for the user may be automatically started without the need for the user to manually enable it.

For example, the user can set his conventional sleep time to 10 p.m., and the start time of the conventional sleep monitoring can be set to 2 hours before the user's conventional sleep time. In other words, 8 p.m. is used as the start time of the conventional sleep monitoring, and sleep monitoring for the user is started at 8 p.m. every day.

Further, the method also includes the step described below.

The sleep monitoring is ended in the case where it is not identified that the user enters the first sleep within a sixth set duration since the sleep monitoring for a user is started.

Optionally, after the sleep monitoring for the user is started, the sleep monitoring is ended if it is not identified that the user enters the first sleep within a period of time. For example, the sixth set duration is set to 8 hours. Then after the sleep monitoring is started, the sleep monitoring is ended if it is not identified that the user enters the first sleep within 8 hours.

Figure 3:
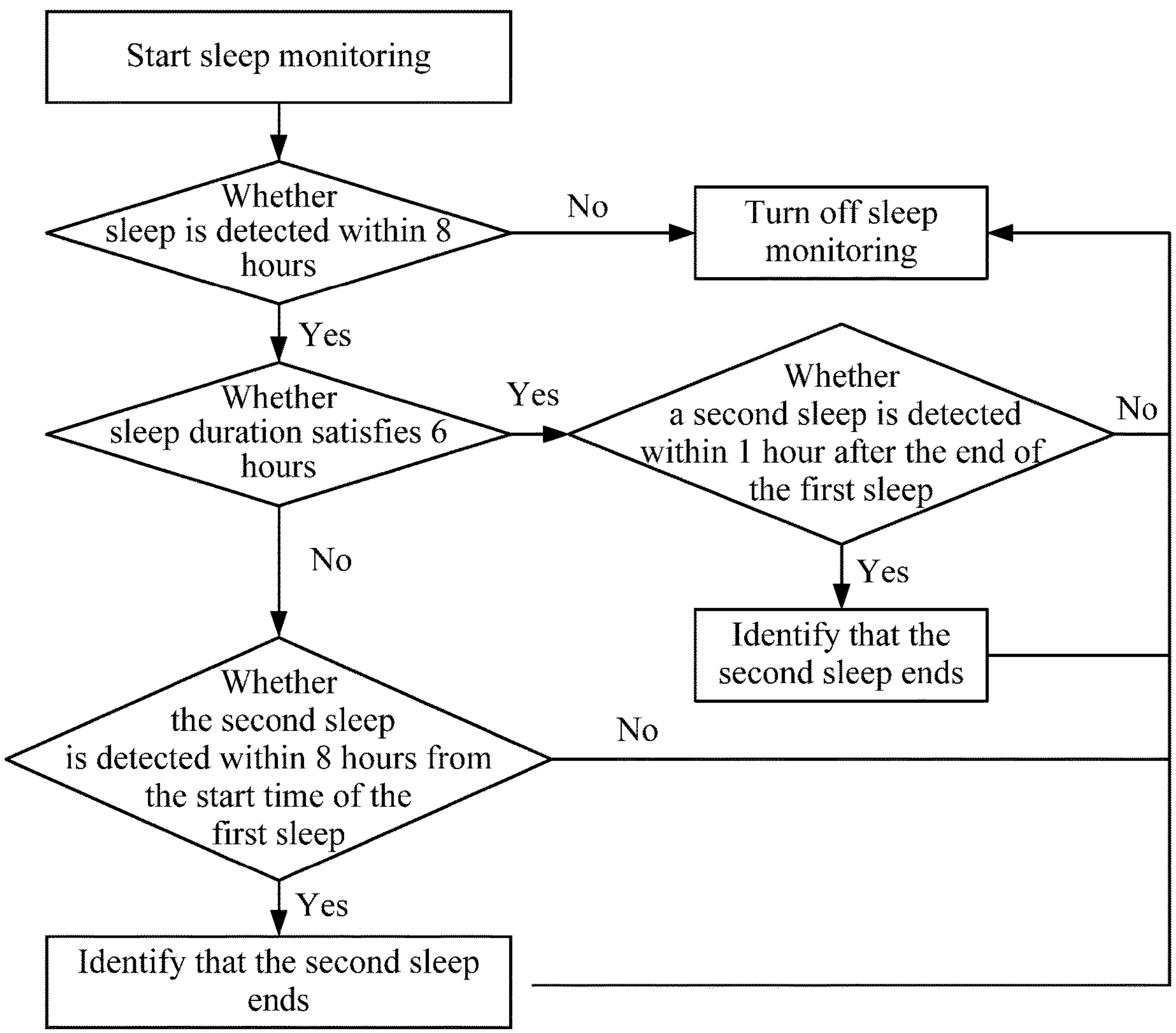
FIG. 3 is a diagram illustrating an overall flow of sleep monitoring according to embodiments of the present invention.

FIG. 3 is a diagram illustrating an overall flow of sleep monitoring according to embodiments of the present invention. As shown in FIG. 3, the fifth set duration is set to 8 hours. Then after the sleep monitoring is started, the sleep monitoring is ended if it is not identified that the user enters the first sleep within 8 hours. If it is identified that the user enters the first sleep within 8 hours, whether the sleep duration satisfies 6 hours at the end of the sleep is determined. If the condition is satisfied, monitoring is continued for 1 hour (that is, the first set duration is 1 hour at this time). If it is not detected that the user falls asleep again during this period, monitoring is turned off at the end of 1 hour. If it is detected that the user enters the first sleep again during this period, the monitoring is turned off at the end of the second sleep. If the first sleep duration of the user does not satisfy 6 hours, monitoring is continued within 8 hours from the start time of the first sleep, that is, the first set duration at this time is the difference between 8 hours (that is, the second set duration) and the duration of the sleep. Similarly, when it is not detected that the user enters the second sleep within the first set duration, the monitoring is turned off at the end of the first set duration. If it is detected that the user enters the second sleep within the first set duration, the monitoring is turned off at the end of the second sleep.

The method for monitoring sleep provided by embodiments of the present invention formulates rules for turning on and off the sleep monitoring and sets a determination method for a user's sleep. In this manner, for the device, power consumption is reduced and service time is prolonged under the condition of ensuring the accuracy of monitoring results.

Embodiments of the present invention also provide a sleep monitoring apparatus that includes at least one processor configured to perform the following steps:

Sleep monitoring for a user is started and sleep monitoring data is acquired.

According to the sleep monitoring data, whether the user enters a first sleep is determined.

According to the sleep monitoring data, whether the user ends the first sleep is determined in the case where it is determined that the user enters the first sleep.

End time of the first sleep is acquired when the user ends the first sleep in the case where it is determined that the user have ended the first sleep.

The sleep monitoring is ended in the case where it is not identified that the user enters a second sleep within a first duration from the end time of the first sleep.

Optionally, the at least one processor is also configured to perform the following steps: Start time of the first sleep when the user enters the first sleep is acquired. A first sleep duration is determined according to the start time of the first sleep and the end time of the first sleep. A first duration is determined according to the first sleep duration.

Optionally, when performing the step of determining the first duration according to the first sleep duration, the at least one processor is also configured to perform the following step:

A difference between a preset third duration and the first sleep duration is determined as the first duration when the first sleep duration is less than a preset second duration.

Optionally, when performing the step of determining the first duration according to the first sleep duration, the at least one processor is also configured to perform the following step:

A duration set by a system or the user is determined as the first duration when the first sleep duration is greater than or equal to a preset second duration.

Optionally, when performing the step of determining whether the user enters the first sleep according to the sleep monitoring data, the processor is specifically configured to perform the following steps:

According to the sleep monitoring data, whether a first sleep event occurs is determined. It is determined that the user enters the first sleep in the case where it is determined that the first sleep event occurs.

Optionally, when performing the step of determining whether the first sleep event occurs according to the sleep monitoring data, the processor is specifically configured to perform the following steps:

Whether the sleep monitoring data are all in a sleep range within a preset fourth duration is determined. It is determined that the first sleep event occurs in the case where it is determined that the sleep monitoring data are all within the sleep range within the preset fourth duration.

In some embodiments, the at least one processor is also configured to perform the following steps:

Start time of the first sleep event and time of occurrence of the first sleep event determined are acquired in the case where it is determined that the first sleep event occurs. Start time of the first sleep is determined according to the start time of the first sleep event and the time of the occurrence of the first sleep event determined. The start time of the first sleep is a time between the start time of the first sleep event and the time of the occurrence of the first sleep event determined.

Optionally, when performing the step of determining whether the user ends the first sleep according to the sleep monitoring data, the processor is specifically configured to perform the following steps:

According to the sleep monitoring data, whether a first wake-up event occurs is determined in the case where it is determined that the user enters the first sleep. It is determined that the user have ended the first sleep in the case where it is determined that the first wake-up event occurs.

Optionally, when performing the step of determining whether the first wake-up event occurs according to the sleep monitoring data, the processor is also configured to perform the following steps:

Whether the sleep monitoring data are all in an awake range within a preset fifth duration is determined. It is determined that the first wake-up event occurs in the case where it is determined that the sleep monitoring data are all within the awake range within the preset fifth duration.

Optionally, the at least one processor is also configured to perform the following steps:

Start time of the first wake-up event and time of occurrence of the first wake-up event determined are acquired in the case where it is determined that the first wake-up event occurs. End time of the first sleep is determined according to the start time of the first wake-up event and the time of the occurrence of the first wake-up event determined. The end time of the first sleep is a time between the start time of the first wake-up event and the time of the occurrence of the first wake-up event determined.

Further, the at least one processor is also configured to perform the following steps:

Within a first duration from the end time of the first sleep, it is determined that the user enters the second sleep according to the sleep monitoring data. Whether the user ends the second sleep is determined according to the sleep monitoring data in the case where it is identified that the user enters the second sleep. The sleep monitoring is ended in the case where it is identified that the user ends the second sleep.

Optionally, the at least one processor is also configured to perform the following steps:

A first sleep duration of the first sleep of the user is determined according to the start time of the first sleep and the end time of the first sleep. A second sleep duration of the second sleep of the user is determined according to start time of the second sleep and end time of the second sleep. The total sleep duration is determined according to the first sleep duration and the second sleep duration. The total sleep duration is the sum of the first sleep duration and the second sleep duration.

Optionally, when performing the step of determining whether the user enters the second sleep according to the sleep monitoring data, the processor is also configured to perform the following steps:

According to the sleep monitoring data, whether a second sleep event occurs within the first duration is determined. It is determined that the user enters the second sleep in the case where it is determined that the second sleep event occurs.

Optionally, when performing the step of determining whether the second sleep event occurs according to the sleep monitoring data, the processor is also configured to perform the following steps:

Whether the sleep monitoring data are all in a sleep range of the user within a preset fourth duration is determined. It is determined that the second sleep event occurs in the case where it is determined that the sleep monitoring data are all within the sleep range within the preset fourth duration.

Further, the at least one processor is also configured to perform the following steps:

Start time of the second sleep event and time of occurrence of the second sleep event determined are acquired in the case where it is determined that the second sleep event occurs. Start time of the second sleep is determined according to the start time of the second sleep event and the time of the occurrence of the second sleep event determined. The start time of the second sleep is a time between the start time of the second sleep event and the time of the occurrence of the second sleep event determined.

Further, when performing the step of determining whether the user ends the second sleep according to the sleep monitoring data, the processor is specifically configured to perform the following steps:

According to the sleep monitoring data, whether a second wake-up event occurs is determined in the case where it is determined that the user enters the second sleep. It is determined that the user ends the second sleep in the case where it is determined that the second wake-up event occurs.

Further, when performing the step of determining whether the second wake-up event occurs according to the sleep monitoring data, the processor is specifically configured to perform the following steps:

Whether the sleep monitoring data are all in an awake range of the user within a preset fifth duration is determined. It is determined that the second wake-up event occurs in the case where it is determined that the sleep monitoring data are all within the awake range within the preset fifth duration.

Further, the at least one processor is also configured to perform the following steps:

Start time of the second wake-up event and time of occurrence of the second wake-up event determined are acquired in the case where it is determined that the second wake-up event occurs. End time of the second sleep is determined according to the start time of the second wake-up event and the time of the occurrence of the second wake-up event determined. The end time of the second sleep is a time between the start time of the second wake-up event and the time of the occurrence of the second wake-up event determined.

In some embodiments, the at least one processor is also configured to perform the following steps:

A set start time for conventional sleep monitoring is acquired.

When performing the step of enabling the sleep monitoring for the user, the processor is specifically configured to perform the following steps:

The sleep monitoring for the user is started at the start time of the conventional sleep monitoring.

In some embodiments, the at least one processor is also configured to perform the following steps:

The sleep monitoring is ended in the case where it is not identified that the user enters the second sleep within a sixth set duration since the sleep monitoring for a user is started.

The sleep monitoring apparatus provided by embodiments of the present invention can execute the method for monitoring sleep according to any embodiment of the present invention and has functional modules and beneficial effects corresponding to the execution methods.

Figure 4:
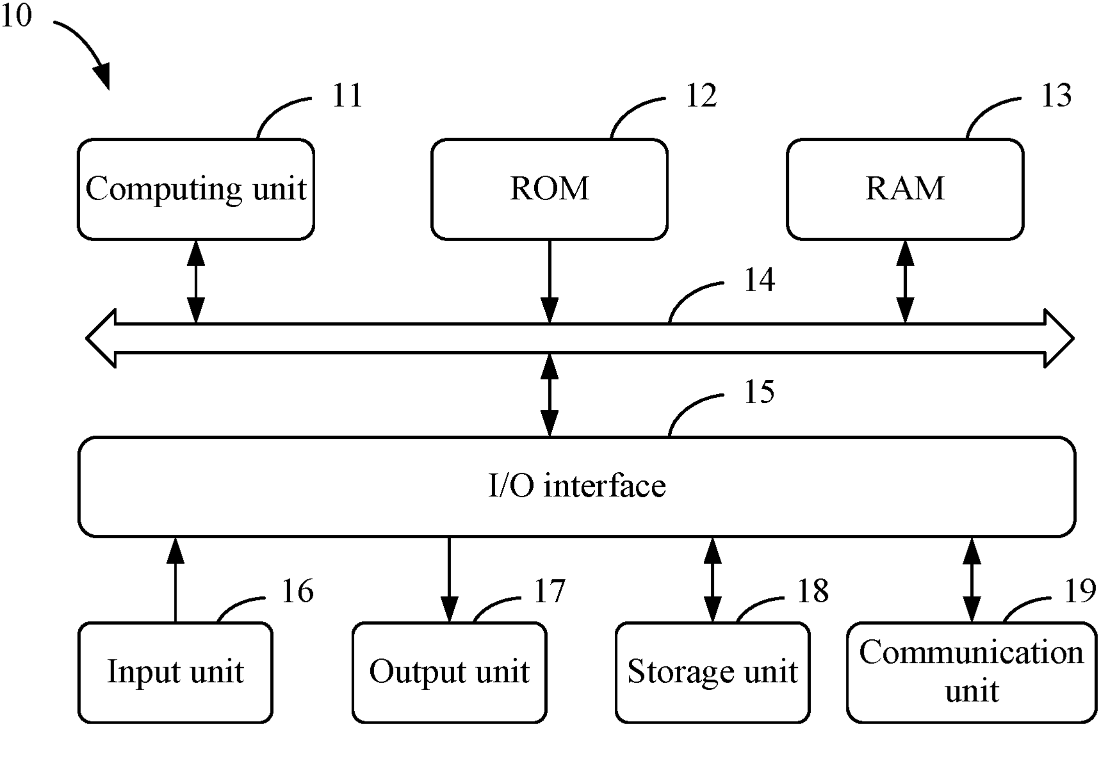
FIG. 4 is a diagram illustrating the structure of an electronic device implementing a method for monitoring sleep according to embodiments of the present invention.

FIG. 4 is a diagram illustrating the structure of an electronic device 10 that can implement embodiments of the present invention. The electronic device is intended to represent various forms of digital computers, for example, a laptop computer, a desktop computer, a worktable, a personal digital assistant, a server, a blade server, a mainframe computer, or other applicable computers. The electronic device may also represent various forms of mobile apparatuses such as a personal digital processing apparatus, a cellular phone, a smart phone, a wearable device (for example, a helmet, glasses, a watch), and other similar computing apparatuses. The components shown herein, their connections and relationships, and their functions, are by way of examples only and are not intended to limit implementations of the inventions described and/or claimed herein.

As shown in FIG. 4, the electronic device 10 includes at least one processor 11 and a memory in a communication connection with the at least one processor 11 such as a read-only memory (ROM) 12 and a random access memory (RAM) 13. The memory stores a computer program executable by the at least one processor. The processor 11 can perform various appropriate actions and processes according to computer programs stored in a read-only memory (ROM) 12 or loaded from a storage unit 18 into a random access memory (RAM) 13. The RAM 13 can also store various programs and data required for the operation of the electronic device 10. The processor 11, the ROM 12, and the RAM 13 are connected to each other through a bus 14. An input/output (I/O) interface 15 is also connected to the bus 14.

Multiple components in the electronic device 10 are connected to the I/O interface 15, including an input unit 16, such as a keyboard or a mouse; an output unit 17, such as various types of displays or speakers; a storage unit 18, such as a magnetic disk or an optical disk; and a communication unit 19, such as a network card, a modem, or a wireless communication transceiver. The communication unit 19 allows the electronic device 10 to exchange information/data with other devices through a computer network such as the Internet and/or various telecommunication networks.

The processor 11 may be various general-purpose and/or special-purpose processing components having processing and computing capabilities. Some examples of the processor 11 include, but are not limited to, a central processing unit (CPU), a graphics processing unit (GPU), various dedicated artificial intelligence (AI) computing chips, various processors running machine learning model algorithms, a digital signal processor (DSP), and any suitable processors, controllers, and microcontrollers. The processor 11 performs various methods and processes described above, such as a method for monitoring sleep.

In some embodiments, the method for monitoring sleep may be implemented as a computer program tangibly embodied in a computer-readable storage medium such as the storage unit 18. In some embodiments, part or all of the computer program may be loaded and/or installed on the electronic device 10 via the ROM 12 and/or the communication unit 19. When the computer program is loaded into the RAM 13 and executed by the processor 11, one or more steps of the sleep monitoring described above may be performed. Alternatively, in other embodiments, the processor 11 may be configured to perform the method for monitoring sleep by any other suitable means (for example, by means of firmware).

Various implementations of the systems and techniques described above herein may be implemented in digital electronic circuitry, integrated circuitry, a field programmable gate array (FPGA), an application specific integrated circuit (ASIC), an application specific standard product (ASSP), a system on chip (SOC), a complex programmable logic device (CPLD), a computer hardware, a firmware, a software, and/or combinations thereof. The various implementations may include an implementation in one or more computer programs that may be executable and/or interpretable on a programmable system including at least one programmable processor. The programmable processor may be special-purpose or general-purpose for receiving data and instructions from a memory system, at least one input apparatus, and at least one output apparatus and transmitting the data and instructions to the memory system, the at least one input apparatus, and the at least one output apparatus.

The computer program for implementing the method of the present invention may be written in any combination of one or more programming languages. These computer programs may be provided to a processor of a general-purpose computer, special-purpose computer, or other programmable data processing apparatus such that the computer programs, when executed by the processor, cause the functions/operations specified in flowcharts and/or block diagrams to be implemented. The computer program may be executed entirely or partly on the machine, as a stand-alone software package partly on the machine and partly on a remote machine, or entirely on the remote machine or server.

In the context of the present invention, a computer-readable storage medium may be a tangible medium that may contain or store a computer program for use by or in conjunction with an instruction execution system, apparatus, or device. The computer-readable storage medium may include, but is not limited to, electronic, magnetic, optical, electromagnetic, infrared, or semiconductor systems, apparatuses, devices, or any suitable combination thereof. Alternatively, the computer-readable storage medium may be a machine-readable signal medium. Concrete examples of the machine-readable storage medium may include an electrical connection based on one or more wires, a portable computer disk, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any appropriate combination thereof.

To provide interaction with a user, the systems and techniques described herein may be implemented on an electronic device. The electronic device has a display device (for example, CRT (cathode ray tube) or LCD (liquid crystal display) monitor) for displaying information to the user; and a keyboard and pointing apparatus (for example, a mouse or a trackball) through which a user can provide input to the electronic device. Other types of apparatuses may also be used for providing interaction with a user. For example, feedback provided for the user may be sensory feedback in any form (for example, visual feedback, auditory feedback, or haptic feedback). Moreover, input from the user may be received in any form (including acoustic input, voice input, or haptic input).

The systems and techniques described herein may be implemented in a computing system including a back-end component (for example, a data server), a computing system including a middleware component (for example, an application server), a computing system including a front-end component (for example, a client computer having a graphical user interface or a web browser through which a user can interact with implementations of the systems and techniques described herein), or a computing system including any combination of such back-end, middleware, or front-end components. Components of a system may be interconnected by any form or medium of digital data communication (for example, a communication network). Examples of the communication network include a local area network (LAN), a wide area network (WAN), a blockchain network, and the Internet.

The computing system may include a client and a server. A client and a server are generally remote from each other and typically interact through a communication network. The relationship between the client and the server arises by virtue of computer programs running on respective computers and having a client-server relationship to each other. The server, which may be a cloud server and is also referred to as a cloud computing server or a cloud host, is a host product in a cloud computing service system. The server solves the problems of difficult management and weak service scalability in the service of a related physical host and a related VPS.

It is to be understood that various forms of processes shown above may be adopted with steps reordered, added, or deleted. For example, the steps described in the present invention may be performed in parallel, sequentially, or in different orders, as long as the desired results of the technical solutions of the present invention can be achieved, and no limitation is imposed herein.

The preceding embodiments do not limit the scope of the present invention. It is to be understood by those skilled in the art that various modifications, combinations, sub-combinations, and substitutions may be performed according to design requirements and other factors. Any modifications, equivalent substitutions, improvements and the like made within the spirit and principle of the present invention are within the scope of the present invention.

What is claimed is:

1. A method for monitoring sleep, applied to a sleep monitoring apparatus comprising an accelerometer and a heart rate sensor, comprising:

starting sleep monitoring for a user and acquiring sleep monitoring data comprising motion signals from the accelerometer and heart rate signals from the heart rate sensor;

determining, according to the sleep monitoring data, whether the user enters a first sleep;

determining, according to the sleep monitoring data, whether the user ends the first sleep in a case where it is determined that the user enters the first sleep;

acquiring end time of the first sleep in a case where it is determined that the user has ended the first sleep, wherein the end time of the first sleep is time when the user ends the first sleep;

maintaining the accelerometer and the heart rate sensor in an active state to monitor for the second sleep during a first duration; and ending the sleep monitoring by deactivating the accelerometer and the heart rate sensor upon expiration of the first duration in a case where it is determined that the user does not enter a second sleep within a first duration from the end time of the first sleep to reduce device power consumption, wherein the method further comprises:

acquiring start time of the first sleep, wherein the start time of the first sleep is time when the user enters the first sleep;

determining a first sleep duration according to the start time of the first sleep and the end time of the first sleep; and determining the first duration according to the first sleep duration, wherein determining the first duration according to the first sleep duration comprises:

determining a difference between a preset third duration and the first sleep duration as the first duration when the first sleep duration is less than a preset second duration, wherein the preset second duration and the preset third duration are predefined values stored in a memory or configured by a user of the device, and determining a duration set by a system or the user as the first duration when the first sleep duration is greater than or equal to a preset second duration.

2. The method of claim 1, wherein determining, according to the sleep monitoring data, whether the user enters the first sleep, comprises:

determining, according to the sleep monitoring data, whether a first sleep event occurs; and determining that the user enters the first sleep in a case where it is determined that the first sleep event occurs.

3. The method of claim 2, wherein determining, according to the sleep monitoring data, whether the first sleep event occurs comprises:

determining whether the sleep monitoring data are all in a sleep range within a preset fourth duration; and determining that the first sleep event occurs in a case where it is determined that the sleep monitoring data are all within the sleep range within the preset fourth duration.

4. The method of claim 3, further comprising: acquiring start time of the first sleep event and time of occurrence of the first sleep event determined in a case where it is determined that the first sleep event occurs; and determining start time of the first sleep according to the start time of the first sleep event and the time of the occurrence of the first sleep event determined, wherein the start time of the first sleep is time between the start time of the first sleep event and the time of the occurrence of the first sleep event determined.

5. The method of claim 1, wherein determining, according to the sleep monitoring data, whether the user ends the first sleep comprises:

determining, according to the sleep monitoring data, whether a first wake-up event occurs in a case where it is determined that the user enters the first sleep; and determining that the user ends the first sleep in a case where it is determined that the first wake-up event occurs.

6. The method of claim 5, wherein determining, according to the sleep monitoring data, whether the first wake-up event occurs comprises:

determining whether the sleep monitoring data are all in an awake range within a preset fifth duration; and determining that the first wake-up event occurs in a case where it is determined that the sleep monitoring data are all within the awake range within the preset fifth duration.

7. The method of claim 6, further comprising: acquiring start time of the first wake-up event and time of occurrence of the first wake-up event determined in a case where it is determined that the first wake-up event occurs; and determining the end time of the first sleep according to the start time of the first wake-up event and the time of the occurrence of the first wake-up event determined, wherein the end time of the first sleep is time between the start time of the first wake-up event and the time of the occurrence of the first wake-up event determined.

8. The method of claim 1, further comprising:

within the first duration from the end time of the first sleep, determining, according to sleep data, whether the user enters the second sleep;

determining, according to the sleep monitoring data, whether the user ends the second sleep in a case where it is determined that the user enters the second sleep; and ending the sleep monitoring when it is determined that the user ends the second sleep.

9. The method of claim 8, further comprising:

determining a first sleep duration of the first sleep of the user according to start time of the first sleep and the end time of the first sleep;

determining a second sleep duration of the second sleep of the user according to start time of the second sleep and end time of the second sleep; and determining a total sleep duration according to the first sleep duration and the second sleep duration;

wherein the total sleep duration is a sum of the first sleep duration and the second sleep duration.

10. The method of claim 8, wherein determining, according to the sleep data, that the user enters the second sleep comprises:

determining, according to the sleep monitoring data, whether a second sleep event occurs; and determining that the user enters the second sleep in a case where it is determined that the second sleep event occurs, wherein determining, according to the sleep monitoring data, whether the second sleep event occurs comprises:

determining whether the sleep monitoring data are all in a sleep range within a preset fourth duration; and determining that the second sleep event occurs in a case where it is determined that the sleep monitoring data are all within the sleep range within the preset fourth duration.

11. The method of claim 10, further comprising: acquiring start time of the second sleep event and time of occurrence of the second sleep event determined in a case where it is determined that the second sleep event occurs; and determining start time of the second sleep according to the start time of the second sleep event and the time of the occurrence of the second sleep event determined, wherein the start time of the second sleep is time between the start time of the second sleep event and the time of the occurrence of the second sleep event determined.

12. The method of claim 8, wherein determining, according to the sleep monitoring data, whether the user ends the second sleep, comprises:

determining, according to the sleep monitoring data, whether a second wake-up event occurs in a case where it is determined that the user enters the second sleep; and determining that the user ends the second sleep in a case where it is determined that the second wake-up event occurs, wherein determining, according to the sleep monitoring data, whether the second wake-up event occurs comprises:

determining whether the sleep monitoring data are all in an awake range within a preset fifth duration; and determining that the second wake-up event occurs in a case where it is determined that the sleep monitoring data are all within the awake range within the preset fifth duration.

13. The method of claim 12, further comprising: acquiring start time of the second wake-up event and time of occurrence of the second wake-up event determined in a case where it is determined that the second wake-up event occurs; and determining end time of the second sleep according to the start time of the second wake-up event and the time of the occurrence of the second wake-up event determined, wherein the end time of the second sleep is time between the start time of the second wake-up event and the time of the occurrence of the second wake-up event determined.

14. The method of claim 1, further comprising:

acquiring a set start time for conventional sleep monitoring;

wherein enabling the sleep monitoring for the user, comprises:

enabling the sleep monitoring for the user at the start time of the conventional sleep monitoring.

15. The method of claim 1, further comprising:

ending the sleep monitoring in a case where it is determined that the user doesn't enter the first sleep within a sixth duration since the sleep monitoring for the user is started.

16. A non-transitory computer-readable storage medium, which is configured to store computer instructions for implementing the method for monitoring sleep of claim 1 when the computer instructions are executed by a processor.

17. An electronic device, comprising:

an accelerometer and a heart rate sensor;

at least one processor; and a memory which is in a communication connection with the at least one processor; wherein the memory stores a computer program executable by the at least one processor, wherein the computer program is configured to, when executed by the at least one processor, cause the at least one processor to execute:

enabling sleep monitoring for a user and acquiring sleep monitoring data comprising motion signals from the accelerometer and heart rate signals from the heart rate sensor;

determining, according to the sleep monitoring data, whether the user enters a first sleep;

determining, according to the sleep monitoring data, whether the user ends the first sleep in a case where it is determined that the user enters the first sleep;

acquiring end time of the first sleep in a case where it is determined that the user has ended the first sleep, wherein the end time of the first sleep is time when the user ends the first sleep;

maintaining the accelerometer and the heart rate sensor in an active state to monitor for the second sleep during a first duration; and ending the sleep monitoring by deactivating the accelerometer and the heart rate sensor upon expiration of the first duration in a case where it is determined that the user does not enter a second sleep within a first duration from the end time of the first sleep to reduce device power consumption, wherein the computer program is configured to, when executed by the at least one processor, cause the at least one processor to execute:

acquiring start time of the first sleep, wherein the start time of the first sleep is time when the user enters the first sleep;

determining a first sleep duration according to the start time of the first sleep and the end time of the first sleep; and determining the first duration according to the first sleep duration, wherein determining the first duration according to the first sleep duration comprises:

determining a difference between a preset third duration and the first sleep duration as the first duration when the first sleep duration is less than a preset second duration, wherein the preset second duration and the preset third duration are predefined values stored in a memory or configured by a user of the device, and determining a duration set by a system or the user as the first duration when the first sleep duration is greater than or equal to a preset second duration.

* * * * *